United States Patent [19]
Hudetz et al.

[11] Patent Number: 6,159,899
[45] Date of Patent: Dec. 12, 2000

[54] HERBICIDAL COMPOSITION AND METHOD OF WEED CONTROL

[75] Inventors: Manfred Hudetz, Rheinfelden, Switzerland; Norbert Nelgen, Jugenheim, Germany

[73] Assignee: Novartis Crop Protection, Inc., Greensboro, N.C.

[21] Appl. No.: 09/160,201

[22] Filed: Sep. 14, 1998

Related U.S. Application Data

[63] Continuation of application No. PCT/EP97/01106, Mar. 5, 1997.

[30] Foreign Application Priority Data

Mar. 15, 1996 [CH] Switzerland ................. 691/96

[51] Int. Cl.⁷ .......... A01N 43/00; A01N 43/64; A01N 43/54
[52] U.S. Cl. .......... 504/130; 504/133; 504/136
[58] Field of Search .......... 504/116, 118, 504/130, 133, 136

[56] References Cited

U.S. PATENT DOCUMENTS 5,002,606  3/1991  Moser et al. .............. 71/118
5,183,492  2/1993  Suchy et al. .............. 504/243

FOREIGN PATENT DOCUMENTS 9809525  3/1998  WIPO .

*Primary Examiner*—S. Mark Clardy
*Assistant Examiner*—Alton Pryor
*Attorney, Agent, or Firm*—Michael P. Morris; William A. Teoli, Jr.

[57] ABSTRACT

A herbicidal composition comprising a compound of formula A

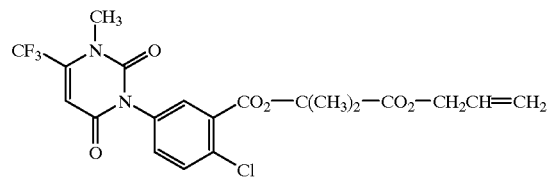

(A)

or an agrochemically acceptable salt thereof and at least one compound from the substance classes of formulae I–VII.

21 Claims, No Drawings

HERBICIDAL COMPOSITION AND METHOD OF WEED CONTROL

This application is a continuation of PCT/EP97/01106 filed Mar. 5, 1997.

The present invention relates to a novel herbicidal composition comprising a herbicidal active ingredient combination that is suitable for the selective control of weeds in crops of useful plants, such as cereals, maize, rice, sugar cane, plantation crops, cotton, potatoes and soybean crops.

The invention relates also to a method of controlling weeds in crops of useful plants and to the use of the novel composition for that purpose.

Herbicidal compositions that comprise the compound of formula A (A)

[chemical structure: CF$_3$-substituted pyrimidinedione with N-CH$_3$, linked to chlorophenyl bearing CO$_2$—C(CH$_3$)$_2$—CO$_2$—CH$_2$CH=CH$_2$]

are described, for example, in U.S. Pat. No. 5,183,492.

It has now surprisingly been shown that a combination of variable proportions of the compound of formula A with at least one compound of formulae I to VII hereinbelow exhibits a herbicidal activity that renders possible effective control, both pre-emergence and post-emergence, of the majority of weeds that occur especially in crops of useful plants, without any significant damage being done to the useful plants.

In accordance with the present invention there is therefore proposed a novel herbicidal composition for selective weed control that comprises, in admixture with one another, the compound of formula A (A)

[chemical structure: same as above]

or an agrochemically acceptable salt thereof as active ingredient, and at least one compound from the substance classes of formula I $$A-SO_2-NH-E \qquad (I),$$

wherein

A is a radical of formula (A1)

[pyridine with CO—N(CH$_3$)$_2$ and CH$_3$]

(A2)

[phenyl with CH$_3$ and CO$_2$CH$_3$]

(A3)

[pyridine with SO$_2$—C$_2$H$_5$ and CH$_3$]

(A4)

[pyrazole with Cl, CO$_2$CH$_3$, CH$_3$, CH$_3$]

(A5)

[thiophene with CH$_3$ and CO$_2$CH$_3$]

(A6)

[phenyl with CH$_3$ and CO$_2$C$_2$H$_5$]

(A7)

[phenyl with CH$_2$— and CO$_2$CH$_3$]

(A8)

[phenyl with CH$_3$ and Cl]

(A9)

[phenyl with CH$_3$ and O—CH$_2$CH$_2$—Cl]

(A10)

[phenyl with CH$_3$ and CH$_2$CH$_2$—CF$_3$]

(A11)

[triazolopyrimidine with CH$_3$ and CH$_3$]

-continued (A12) 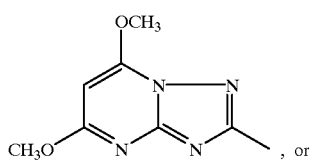, or (A13) 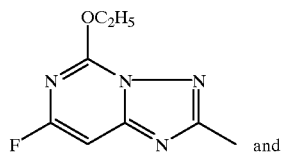 and

E is a radical of formula (E1) 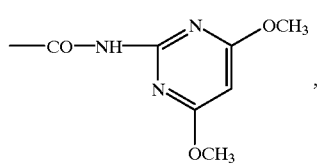, (E2) 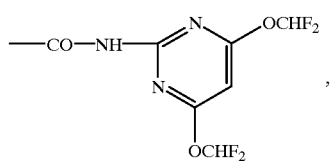, (E3) 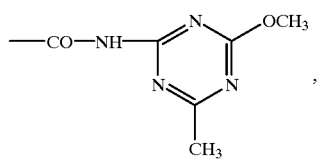, (E4) 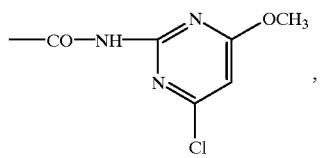, (E5) 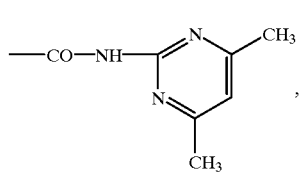, (E6) 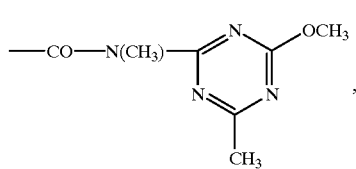, -continued (E7) 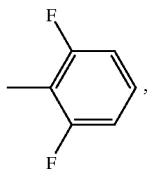, (E8) 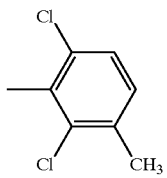 or (E9) 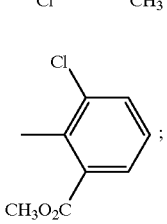;

of formula II $$\underset{U \diagdown V}{N} \diagup \underset{W}{\overset{Y}{\diagdown}}$$ (II)

wherein

U-V is a radical of formula $CR_1=N$, $N=CR_1$ or $NR_1CO$ wherein $R_1$ is —$NH_2$, —$NHC_3H_7$—i, —$NHC(CH_3)_2CN$, —$NHC_4H_9$—t, —$NHC_2H_5$, —$SCH_3$, —$CH_3$, —Cl, $C_6H_{11}$,

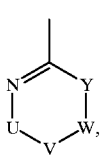 or 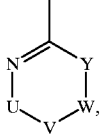,

W-Y is a radical of formula $CR_2=N$, $N=CR_2$, $NR_2CO$, NH or $CR_2=CR_3$ wherein $R_2$ is hydrogen, —Cl, —$NH_2$, —$NHC_3H_7$—i, —$NHC_2H_5$ or —$NHC(CH_3)_3$ and $R_3$ is —$NH_2$, —$NHCH_3$ or —O—CO—$SC_8H_{17}$, and R is —Cl, —$SCH_3$, —$C_4H_9$—t,

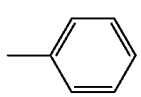

or hydrogen;
of formula III
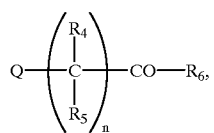 (III)
wherein
n is 0 or 1,
$R_4$ is hydrogen,
$R_5$ is hydrogen, —$CH_3$ or —$NH_2$,
$R_6$ is hydroxy, —$OC_2H_5$, —O—$C(CH_3)_2$—$CO_2C_2H_5$, —$NHSO_2CH_3$, —$OCH_3$, —$OC_4H_9$—n, —$OCH_2$—C≡CH or —$OC_2H_4$—O—N=$C(CH_3)_2$ and
Q is a radical of formula
—$CH_2CH_2$—P(O)(OM)$CH_3$ (Q1)
or
—$NHCH_2$—P(O)(OM)$_2$ (Q2)
wherein M is an alkali metal, ammonium, alkylammonium, sulfonium or alkylsulfonium,
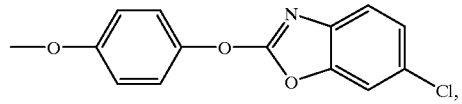 (Q3)
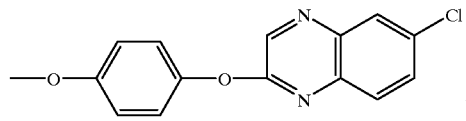 (Q4)
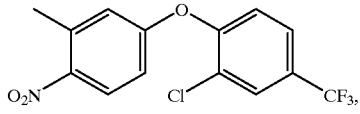 (Q5)
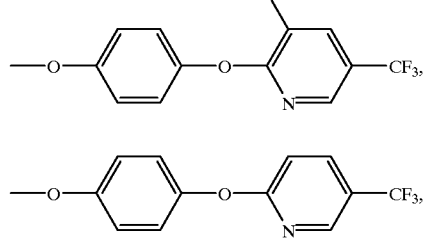 (Q6), (Q7)
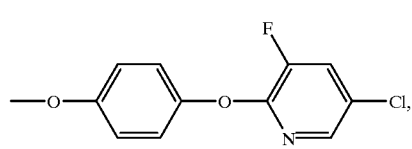 (Q8)
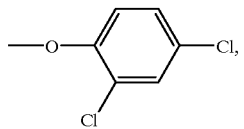 (Q9)
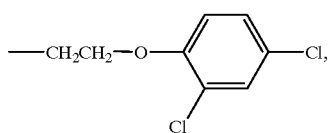 (Q10)
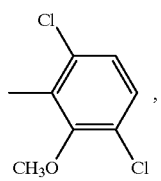 (Q11)
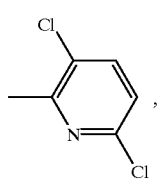 (Q12)
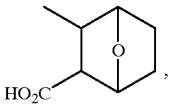 (Q13)
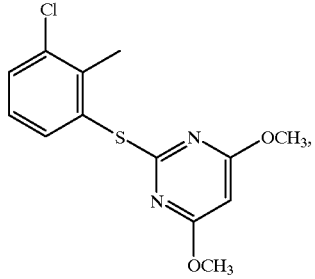 (Q14)
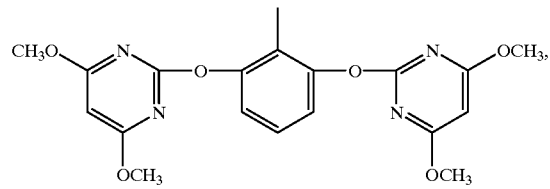 (Q15)
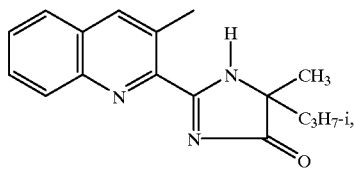 (Q16)

-continued (Q17)

[structure: pyridine with H5C2, CH3, connected to imidazolinone with CH3, C3H7-i]

(Q18)

[structure: pyridine with CH3, connected to imidazolinone with CH3, C3H7-i] or (Q19)

[structure: CH3—O—CH2— substituted pyridine with CH3, connected to imidazolinone with CH3, C3H7-i];

of formula IV (IV)

[structure: phenyl ring with positions 2,3,4,5,6 bearing R10, R9, R8, R7 and X—R11]

wherein

R$_7$ is 2-NO$_2$, 2-Br or 2-F,

R$_8$ is 6-NH$_2$, 6-Br or 6-NO$_2$, or

R$_8$ and R$_7$ together form a radical of formula —C(CH$_3$)$_2$—CH(OC$_2$H$_5$)O— that bridges the 2- and 3-positions of the phenyl radical, the carbon atom of that radical being linked to the 2-position and the oxygen atom of that radical being linked to the 3-position, R$_9$ is 3-CH$_3$, 4-CF$_3$, 4-CN or 5-SCH$_2$COOCH$_3$, R$_{10}$ is hydrogen, 4-CH$_3$ or 4-Cl, X is —O—, —NH—, —NC$_3$H$_7$(n)— or —NC$_2$H$_5$— and R$_{11}$ is hydrogen, —CH(C$_2$H$_5$)$_2$, —C$_3$H$_7$—n, —CH$_2$—C(CH$_3$)=CH$_2$, —CO—C$_8$H$_{17}$—n, —CO—C$_7$H$_{15}$—n or —SO$_2$CH$_3$, or R$_{11}$ and X together form a radical

[structure: bicyclic with N—N, S, =N—CH3, =O];

of formula V $$Z-\underset{R_{12}}{N}-CO-R_{13},$$
(V)

wherein

Z is a radical of formula (Z1) [2,3-dichloro-6-methylphenyl]

(Z2) [3,4-dichlorophenyl]

(Z3) [3-CF3-phenyl]

(Z4) [2-CH3, 3-C2H5-phenyl]

(Z5) [2,6-diethylphenyl]

(Z6) [phenyl]

(Z7) [thiophene with 3-CH3, 4-CH3, 2-CH3]

(Z8) —CH$_2$—C$_3$H$_7$-i, (Z9) —C$_3$H$_7$-n, (Z10) —C$_4$H$_9$-n,

-continued (Z11)

[structure: methylcyclohexane]

(Z12)

[structure: 3-methylphenyl-O-CONH-phenyl]

(Z13)

[structure: 3-methylphenyl-O-CONH-(4-methylphenyl)]

(Z14)

—CH$_2$-(2-chlorophenyl)

(Z15)

(4-fluorophenyl)— or (Z16)

—C$_3$H$_7$-i,

R$_{12}$ is hydrogen, —CH$_2$OCH$_3$, —CH$_2$OC$_2$H$_5$, —CH(CH$_3$)CH$_2$OCH$_3$, —C$_3$H$_7$—i, —CH$_2$—C$_3$H$_7$—i, —C$_3$H$_7$—n, —CH$_3$, —C$_2$H$_5$ or —CH$_2$—CH=CH$_2$ or R$_{12}$ forms together with Z a radical of formula

[structures: benzodioxane-type, spiro cyclopentane dioxolane, spiro cyclohexane dioxolane, dimethyl dioxolanes, furan-dioxolane]

and

R$_{13}$ is —N(CH$_3$)$_2$, —N(OCH$_3$)CH$_3$, —CH$_2$Cl, —CHCl$_2$, —SC$_2$H$_5$, —SC$_3$H$_7$—n, —OCH$_3$, —OC$_2$H$_5$, —CH$_2$—CH=CH$_2$ or

—CH$_2$—O—(1,3,4-thiadiazole)—C$_3$F or

R$_{13}$ forms together with R$_{12}$ a radical of formula
—O—CH$_2$—C(CH$_3$)$_2$—, —CH$_2$—CH(CH$_2$Cl)—CHCl— or —SO$_2$—NH-(2-methylphenyl);

of formula VI (VI)

[structure: cyclohexenone with R$_{14}$, OH, C(=X$_1$)R$_{15}$]

wherein
R$_{14}$ is hydrogen or —CH$_2$—CH(CH$_3$)—SC$_2$H$_5$,
R$_{15}$ is —C$_2$H$_5$, —C$_3$H$_7$—n or

[structure: 2-methyl-5-chloro-phenyl-SO$_2$CH$_3$]

and
X$_1$ is =O, =NOC$_2$H$_5$ or =NOCH$_2$—CH=CHCl;
or of formula VII (VII)

CH$_3$—N$^\oplus$(pyridyl-pyridyl)N$^\oplus$—CH$_3$  2X$_2^\ominus$, wherein
X$_2^\ominus$ is Cl$^\ominus$ or CH$_3$SO$_3^\ominus$.

It is extremely surprising that the combination of the compound of formula A with at least one compound from the substance classes of formulae I to VII exceeds the additive effect on the weeds to be controlled that is to be expected in principle, and thus broadens the range of activity of the two preparations especially in the following two respects:

First, the rates of application of the individual compounds are reduced while the good action remains unchanged. Secondly, the composition according to the invention achieves a high degree of weed control even where the individual substances have become no longer usable agronomically at low rates of application. The result is a substantial broadening of the weed spectrum and an additional increase in selectivity for the crops of useful plants, which is desirable and necessary should an unintentional overdose of active ingredient be applied.

The herbicidal mixture according to the invention can be used against a large number of agronomically important weeds, such as Veronica, Galium, Papaver, Solanum, Chenopodium, Amaranthus, Xanthium, Abutilon, Ambrosia, Sagitaria, Setaria, Digitaria, Echinochloa, Ipomoea, Cassiastora, *Datura stramonium, Sesbania exaltata* and *Sida spinosa* in crops of useful plants. It has also been shown that after application of the compositions according to the invention the compound of formula A contained therein is broken down more rapidly in the useful plants treated, especially maize, than metolachlor, which is an important advantage.

The compositions according to the invention are suitable for all methods of application customary in agriculture, such as pre-emergence application, post-emergence application and seed dressing.

The herbicidal mixture according to the invention is suitable especially for weed control in crops of useful plants such as cereals, sugar cane, plantation crops (TVM), rice, cotton, soybeans, potatoes and, especially, maize, and also for dessication (drying out) or defoliation, for example for the purpose of facilitating harvesting, for example in cotton and potato crops.

"Crops" is also to be understood as meaning crops that have been made tolerant to herbicides and classes of herbicides by conventional breeding or genetic engineering methods.

The active ingredient combination according to the invention comprises the compound of formula A and the compound or compounds from the substance classes of formulae I to VII in any mixing ratio, but usually with an excess of one component over the other(s). Preferred mixing ratios of the compound of formula A with its mixing partners are generally from 100:1 to 1:100.

Of the above-mentioned herbicidal compositions, preference is given to those in which in the compounds of formula II $R_1$ is —$NHC_3H_7$—i, —$NHC(CH_3)_2CN$, —$NHC_4H_9$—t, —$NHC_2H_5$, —$SCH_3$, —$CH_3$, —Cl,

[phenyl] or [3-CF₃-phenyl]

and
W-Y is a radical of formula $CR_2$=N, N=$CR_2$,

—NC(O)R₂ or $CR_2$=$CR_3$.

Of the above-mentioned herbicidal compositions preference is given also to those that comprise in addition to the compound of formula A at least one compound from the substance classes of formula I $$A-SO_2-NH-E \quad (I),$$

wherein

A is a radical of formula

[pyridyl-CO—N(CH₃)₂] (A1)

[phenyl-CO₂CH₃] (A2)

[pyridyl-SO₂—C₂H₅] (A3)

[Cl-pyrazole-CO₂CH₃ with CH₃, N-CH₃] (A4)

[methylthiophene-CO₂CH₃] (A5)

[phenyl-CO₂C₂H₅] (A6)

[phenyl-CH₂—CO₂CH₃] (A7)

[phenyl-Cl] (A8)

[phenyl-O—CH₂CH₂—Cl] (A9)

[phenyl-CH₂CH₂—CF₃] (A10)

[triazolopyrimidine with CH₃] (A11)

-continued (A12) 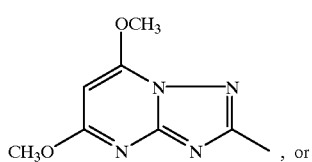, or (A13) 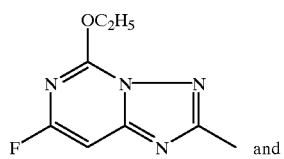 and

E is a radical of formula (E1) 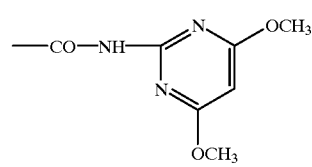, (E2) 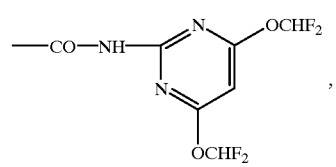, (E3) 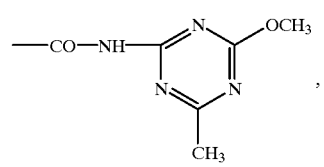, (E4) 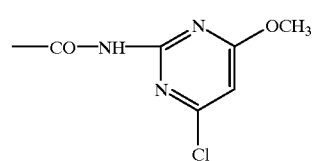, (E5) 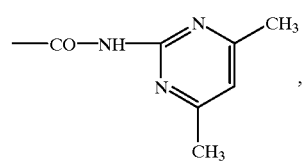, (E6) 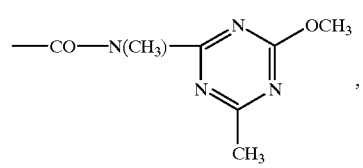, (E7) 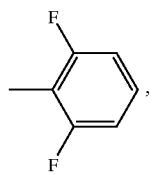, (E8) 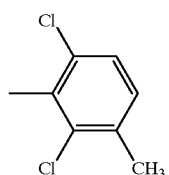 or (E9) 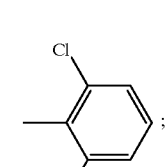;

of formula II

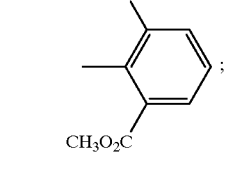 (II)

wherein

U-V is a radical of formula $CR_1 = N$ or $N = CR_1$ wherein
$R_1$ is —$NHC_3H_7$—i, —$NHC(CH_3)_2CN$, —$NHC_4H_9$—t, —$NHC_2H_5$ or —Cl, W-Y is a radical of formula $CR_2 = N$, $N = CR_2$ or $CR_2 = CR_3$ wherein $R_2$ is hydrogen, —$NHC_3H_7$—i, —$NHC_2H_5$ or —$NHC(CH_3)_3$ and $R_3$ is —O—CO—$SC_8H_{17}$, and R is —Cl, —$SCH_3$ or

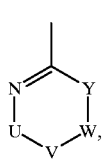;

of formula III

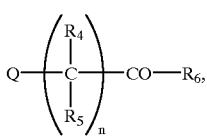 (III)

wherein n is 0 or 1, $R_4$ is hydrogen, $R_5$ is hydrogen, —$CH_3$ or —$NH_2$,
$R_6$ is hydroxy, —$OC_2H_5$, —$OC_4H_9$—n or —$OC_2H_4$—O—N=C$(CH_3)_2$ and
Q is a radical of formula

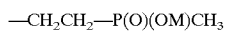   (Q1)

or

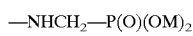   (Q2)

wherein M is an alkali metal, ammonium, alkylammonium, sulfonium or alkylsulfonium,

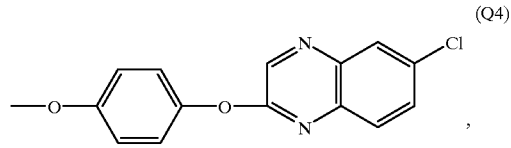   (Q4)

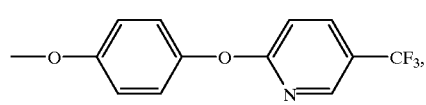   (Q7)

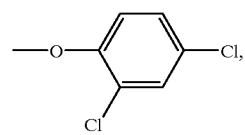   (Q9)

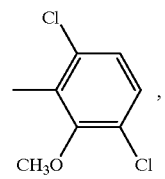   (Q11)

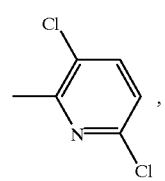   (Q12)

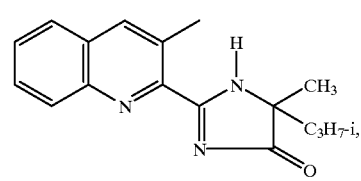   (Q16)

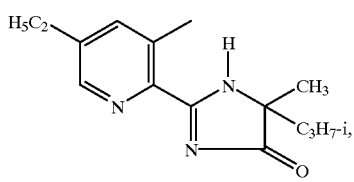   (Q17)

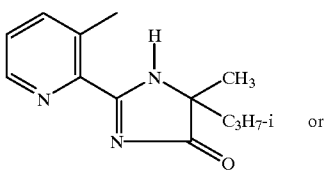   (Q18)

or

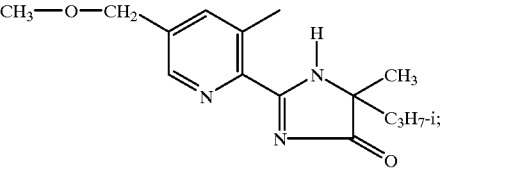   (Q19)

of formula IV

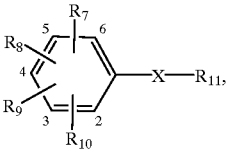   (IV)

wherein $R_7$ is 2-$NO_2$ or 2-Br,
$R_8$ is 6-$NH_2$ or 6-Br,
$R_9$ is 3-$CH_3$, 4-$CF_3$ or 4-CN,
$R_{10}$ is 4-$CH_3$,
X is —O—, —NH— or —$NC_3H_7$—n and
$R_{11}$ is hydrogen, —$CH(C_2H_5)_2$ or —$C_3H_7$—n;

of formula V

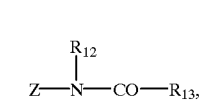   (V)

wherein

Z is a radical of formula

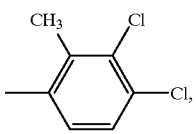   (Z1)

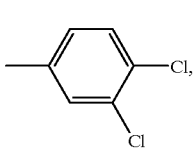   (Z2)

-continued (Z3) 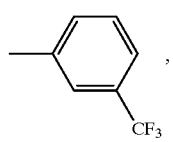

(Z4) 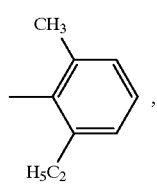

(Z5) 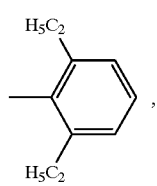

(Z6) 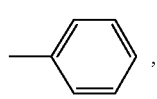

(Z7) 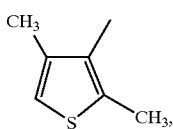

(Z8) —CH₂—C₃H₇-i, (Z9) —C₃H₇-n, (Z10) —C₄H₉-n, (Z11) 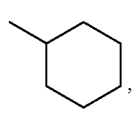

(Z15) 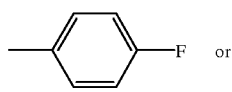

(Z16) —C₃H₇-i,

R₁₂ is hydrogen, —CH₂OCH₃, —CH₂OC₂H₅, —CH(CH₃)CH₂OCH₃, —C₃H₇—i, —CH₂—C₃H₇—i, —C₃H₇—n, —CH₃, —C₂H₅ or —CH₂—CH=CH₂ or R₁₂ forms together with Z a radical of formula

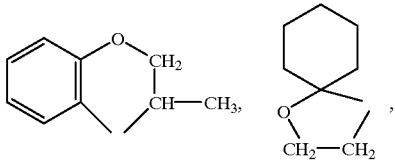

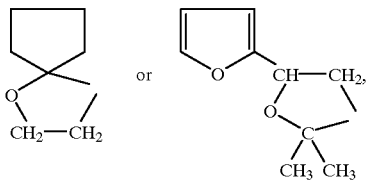

and

R₁₃ is —N(CH₃)₂, —N(OCH₃)CH₃, —CH₂Cl₂, —CHCl₂, —SC₂H₅, —SC₃H₇—n, —OCH₃, —OC₂H₅, —CH₂—CH=CH₂ or

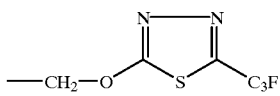

or

R₁₃ forms together with R₁₂ a radical of formula —O—CH₂—C(CH₃)₂—, —CH₂—CH(CH₂Cl)—CHCl— or

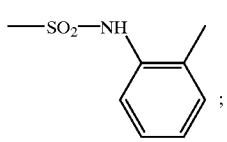

of formula VI

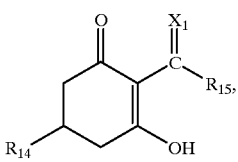

(VI)

wherein
R₁₄ is hydrogen,
R₁₅ is —C₃H₇—n or

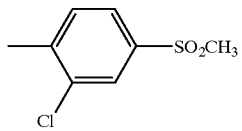

and
X₁ is =O or =NOC₂H₅;

or of formula VII

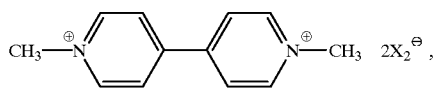   (VII)

wherein $X_2^\ominus$ is $Cl^\ominus$ or $CH_3SO_3^\ominus$.

The following combinations have proved to be especially effective active ingredient mixtures:

compound of formula A+atrazine, compound of formula A+fluthiacet, compound of formula A+cyanazine, compound of formula A+flumetsulam, compound of formula A+metolachlor (racemate), compound of formula A+metolachlor (S-enantiomer), compound of formula A+metosulam, compound of formula A+nicosulfuron, compound of formula A+pendimethalin, compound of formula A+rimsulfuron, compound of formula A+terbuthylazine, compound of formula A+2,4-D, compound of formula A+bromoxynil, compound of formula A+dicamba, compound of formula A+halosulfuron, compound of formula A+primisulfuron, compound of formula A+prosulfuron, compound of formula A+simazine, compound of formula A+sulcotrione, compound of formula A+acetochlor, compound of formula A+alachlor, compound of formula A+ametryn, compound of formula A+bentazon, compound of formula A+butylate, compound of formula A+clopyralid, compound of formula A+dimethenamid (racemate), compound of formula A+dimethenamid (S-enantiomer), compound of formula A+EPTC, compound of formula A+thifensulfuron, compound of formula A+trifluralin, compound of formula A+cloransulam-methyl, compound of formula A+terbutryn, compound of formula A+glyphosate, compound of formula A+glufosinate and compound of formula A+sulfosate.

Of those the following active ingredient combinations are of particular importance:

compound of formula A+primisulfuron+dicamba, compound of formula A+prosulfuron+dicamba, compound of formula A+primisulfuron+bromoxynil, compound of formula A+primisulfuron+pyridate, compound of formula A+prosulfuron+bromoxynil, compound of formula A+atrazine+metolachlor (S-enantiomer), compound of formula A+terbuthylazine+metolachlor (S-enantiomer) and compound of formula A+prosulfuron+pyridate and especially compound of formula A+atrazine, compound of formula A+cyanazine, compound of formula A+flumetsularn, compound of formula A+metolachlor (racemate), compound of formula A+metolachlor (S-enantiomer), compound of formula A+metosulam, compound of formula A+pendimethalin, compound of formula A+simazine, compound of formula A+terbuthylazine, compound of formula A+acetochlor, compound of formula A+alachlor, compound of formula A+dimethenamid, compound of formula A+cloransulam-methyl, compound of formula A+glyphosate, compound of formula A+glufosinate and compound of formula A+sulfosate.

Some of the last group of active ingredient combinations are suitable for use with a safener. This results especially in combinations such as compound of formula A+metolachlor (racemate)+compound of formula V

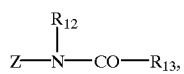   (V)

wherein

Z is $-CH_2-CH=CH_2$, $R_{12}$ is $-CH_2-CH=CH_2$ or $R_{12}$ forms together with Z a radical of formula

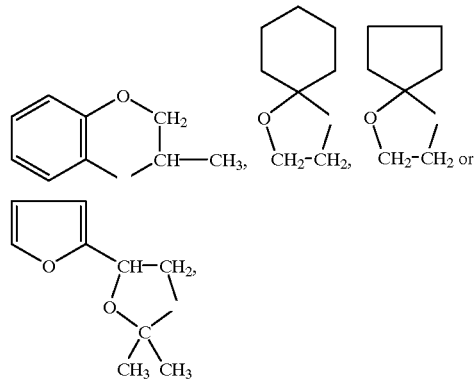

and $R_{13}$ is $-CHCl_2$; compound of formula A+metolachlor (S-enantiomer)+compound of formula V

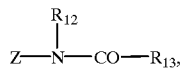   (V)

wherein

Z is $-CH_2-CH=CH_2$, $R_{12}$ is $-CH_2-CH=CH_2$ or $R_{12}$ forms together with Z a radical of formula

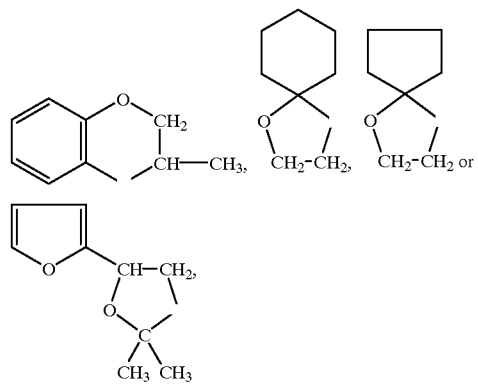

and $R_{13}$ is $-CHCl_2$; compound of formula A+acetochlor+compound of formula V

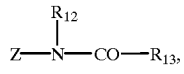   (V)

wherein

Z is $-CH_2-CH=CH_2$, $R_{12}$ is $-CH_2-CH=CH_2$ or $R_{12}$ forms together with Z a radical of formula

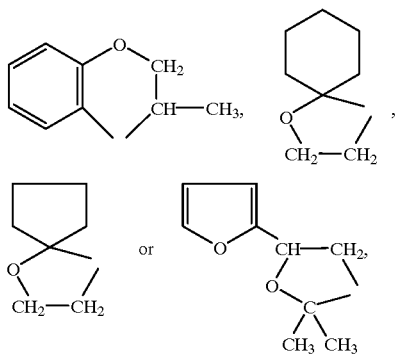

and $R_{13}$ is —$CHCl_2$; and compound of formula A+dimethenamid+compound of formula V $$Z-N(R_{12})-CO-R_{13}, \quad (V)$$

wherein

Z is —$CH_2$—CH=$CH_2$, $R_{12}$ is —$CH_2$—CH=$CH_2$ or $R_{12}$ together with Z forms a radical of formula

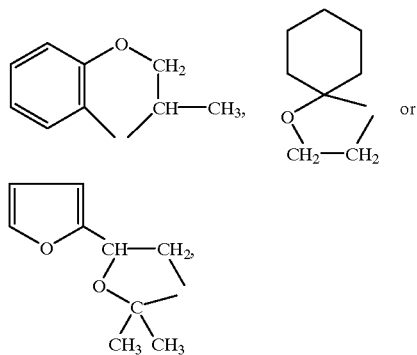

and $R_{13}$ is —$CHCl_2$; especially compound of formula A+metolachlor (racemate)+benoxacor and compound of formula A+metolachlor (S-enantiomer)+benoxacor; and also compound of formula A+EPTC+compound of formula V $$Z-N(R_{12})-CO-R_{13}, \quad (V)$$

wherein

—Z is —$CH_2$—CH—$CH_2$, $R_{12}$ is —$CH_2$—CH=$CH_2$ or $R_{12}$ forms together with Z a radical of formula

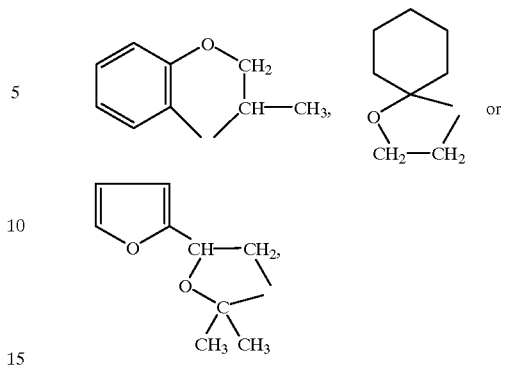

and $R_{13}$ is —$CHCl_2$; and compound of formula A+butylate+compound of formula V $$Z-N(R_{12})-CO-R_{13}, \quad (V)$$

wherein

Z is —$CH_2$—CH=$CH_2$, $R_{12}$ is —$CH_2$—CH=$CH_2$ or $R_{12}$ forms together with Z a radical of formula

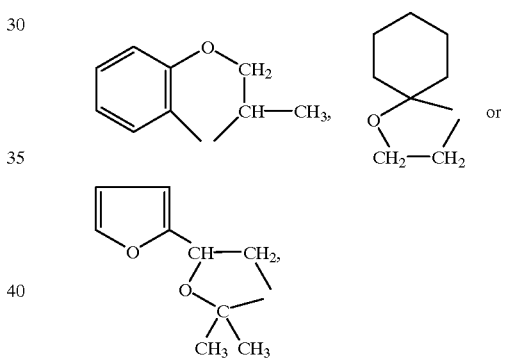

and $R_{13}$ is —$CHCl_2$.

The above-mentioned active ingredient combinations are suitable especially for use in maize.

The following active ingredient combinations may be used specifically for maize that is resistant to imidazolinone herbicides:

compound of formula A+imazaquin, compound of formula A+imazethapyr, compound of formula A+glyphosate, compound of formula A+glufosinate, compound of formula A+sulfosate, compound of formula A+chlorimuron ethyl, compound of formula A+imazapyr, compound of formula A+bensulfuron, compound of formula A+chlorsulfuron, compound of formula A+metsulfuron methyl, compound of formula A+sulfometuron methyl, compound of formula A+triasulfuron and compound of formula A+tribenuron methyl or also compound of formula A+imazaquin and compound of formula A+imazethapyr.

Other active ingredient combinations according to the invention may be used, for example in potato and cotton crops, as dessicators or defoliants for the purpose of facilitating harvesting, for example compound of formula A+glufosinate and compound of formula A+fluthiacet, in sugar cane for example compound of formula A+ametryn, or in no-till-maize and plantation crops (TVM), for example compound of formula A+glufosinate, compound of formula A+glyphosate, compound of formula A+sulfosate and compound of formula A+paraquat, also compound of formula A+sethoxydim, compound of formula A+propaquizafop, compound of formula A+quizalofop and compound of formula A+fluazifop.

The above-mentioned active ingredients are described and characterised in "The Pesticide Manual", Tenth Edition, 1994, Crop Protection Publications, and other customary agronomical technical literature. The compound of formula A is described, for example, in U.S. Pat. No. 5,183,492.

The optical isomer (S-enantiomer) of metolachlor suitable in accordance with the invention is aRS, 1'S(−)-N-(1'-methyl-2'-methoxyethyl)-N-chloroacetyl-2-ethyl-6-methylaniline of formula Va

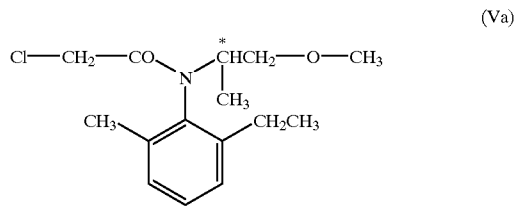

(Va)

and also its agrochemically acceptable salts, which are described, for example, in U.S. Pat. No. 5,002,606.

The rate of application of the active ingredients may vary within wide limits and depends on the nature of the soil, the type of use (pre- or post-emergence; seed dressing; application to the seed furrow; no tillage application etc.), the crop plant, the weed to be controlled, the prevailing climatic conditions, and other factors determined by the type of use, time of use and target crop. Generally, the active ingredient mixture according to the invention can be applied at a rate of application of from 50 to 4000 g of active ingredient mixture/ha.

In the composition according to the invention, the component of formula A is present in a ratio by weight of from 1:100 to 1:0.001 to a compound from the substance classes of formulae I to VII.

If the composition comprises a safener, the ratio by weight of herbicide of formula (A) to safener is preferably from 1:5 to 30:1.

The compositions according to the invention may be used in unmodified form, that is to say as obtained in the synthesis, but they are preferably formulated in customary manner together with the adjuvants customarily employed in formulation technology, e.g. into emulsifiable concentrates, provided sulfonylureas are not present, directly sprayable or dilutable solutions, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, that is to say the compositions, preparations or mixtures comprising the compounds (active ingredients) of formulae A and I, II, III, IV, V, VI or VII, and, as appropriate, a safener and/or one or more solid or liquid formulation adjuvants, are prepared in a manner known per se, e.g. by homogeneously mixing and/or grinding the active ingredients with the formulation adjuvants, for example solvents or solid carriers. It is also possible in addition to use surface-active compounds (surfactants) in the preparation of the formulations.

Suitable solvents are: aromatic hydrocarbons, preferably the fractions containing 8 to 12 carbon atoms, such as mixtures of alkylbenzenes, for example xylene mixtures or alkylated naphthalenes; aliphatic and cycloaliphatic hydrocarbons, such as paraffins, cyclohexane or tetrahydronaphnialene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and their esters, such as rape oil, castor oil or soybean oil; and where appropriate also silicone oils.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are, for example, calcite or sand. In addition, a great number of pregranulated materials of inorganic or organic nature can be used, e.g. especially dolomite or pulverised plant residues.

Depending on the nature of the active ingredient to be formulted, suitable surface-active compounds are non-ionic, cationic and/or anionic surfactants having good emulsifying, dispersing and wetting properties. The term "surfactants" will also be understood as comprising mixtures of surfactants.

Both water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurine salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, the alkyl moiety of acyl radicals also being included, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which may also be used in the compositions according to the invention, are described inter alia in "McCutcheons's Detergents and Emulsifiers Annual", MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980–1981.

The herbicidal formulations usually contain from 0.1 to 99 %, especially from 0.1 to 95 %, of an active ingredient mixture of the compound of formula A with the compounds of formulae I, II, III, IV, V, VI or VII, from 1 to 99 % of a solid or liquid adjuvant, and from 0 to 25%, especially from 0.1 to 25%, of a surfactant.

Whereas commercial products will preferably be formulated as concentrates, the end user will normally employ dilute formulations.

The compositions may also comprise further auxiliaries, such as stabilisers, for example vegetable oils or epoxidised vegetable oils (epoxidised coconut oil, rape oil or soybean oil), antifoams, for example silicone oil, preservatives, viscosity regulators, binders and tackifiers, as well as fertilisers or other active ingredients.

Preferred formulations have especially the following compositions (throughout, percentages are by weight):
Emulsifiable concentrates:
  active ingredient mixture: 1 to 90%, preferably 5 to 20%
  surface-active agent: 1 to 30%, preferably 10 to 20%
  liquid carrier: 5 to 94%, preferably 70 to 85%
Dusts:
  active ingredient mixture: 0.1 to 10%, preferably 0.1 to 5%
  solid carrier 99.9 to 90%, preferably 99.9 to 99%
Suspension concentrates:
  active ingredient mixture: 5 to 75%, preferably 10 to 50%
  water: 94 to 24%, preferably 88 to 30%
  surface-active agent: 1 to 40%, preferably 2 to 30%
Wettable powders:
  active ingredient mixture: 0.5 to 90%, preferably 1 to 80%
  surface-active agent: 0.5 to 20%, preferably 1 to 15%
  solid carrier: 5 to 95%, preferably 15 to 90%
Granules:
  active ingredient mixture: 0.1 to 30%, preferably 0.1 to 15%
  solid carrier: 99.5 to 70%, preferably 97 to 85%

The following Examples further illustrate, but do not limit, the invention.

FORMULATION EXAMPLES

Mixtures of compounds of formulae A, I, II, III IV, V, VI or VII (throughout, percentages are by weight)

| F1. Emulsifiable concentrates | a) | b) | c) | d) |
|---|---|---|---|---|
| mixture of a compound of formula A with one of the compounds of formulae I to VII | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| mixture of a compound of formula A with one of the compounds of formulae I to VII | 5% | 10% | 50% | 90% |
| 1-methoxy-3-(3-methoxypropoxy)-propane | — | 20% | 20% | — |
| polyethylene glycol MW 400 | 20% | 10% | — | — |
| N-methyl-2-pyrrolidone | — | — | 30% | 10% |
| aromatic hydrocarbon mixture $C_9$–$C_{12}$ | 75% | 60% | — | — |

These solutions are suitable for application in the form of microdrops.

| F3. Wettable powders | a) | b) | c) | d) |
|---|---|---|---|---|
| mixture of a compound of formula A with one of the compounds of formulae I to VII | 5% | 25% | 50% | 80% |
| sodium lignosulfonate | 4% | — | 3% | — |
| sodium lauryl sulfate | 2% | 3% | — | 4% |
| sodium diisobutylnaphthalene sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the additives and the mixture is thoroughly ground in a suitable mill, affording wettable powders which can be diluted with water to give suspensions of any desired concentration.

| F4. Coated granules | a) | b) | c) |
|---|---|---|---|
| mixture of a compound of formula A with one of the compounds of formulae I to VII | 0.1% | 5% | 15% |
| highly dispersed silicic acid | 0.9% | 2% | 2% |

-continued

| F4. Coated granules | a) | b) | c) |
|---|---|---|---|
| inorganic carrier (diameter 0.1–1 mm) for example CaCO$_3$ or SiO$_2$ | 99.0% | 93% | 83% |

The active ingredient is dissolved in methylene chloride and the solution is sprayed onto the carrier, and the solvent is subsequently evaporated off in vacuo.

| F5. Coated granules | a) | b) | c) |
|---|---|---|---|
| mixture of a compound of formula A with one of the compounds of formulae I to VII | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1–1 mm) for example CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| mixture of a compound of formula A with one of the compounds of formulae I to VII | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| mixture of a compound of formula A with one of the compounds of formulae I to VII | 0.1% | 1% | 5% |
| talcum | 39.9% | 49% | 35% |
| kaolin | 60.0% | 50% | 60% |

Ready-for-use dusts are obtained by mixing the active ingredient with the carriers, and grinding the mixture in a suitable mill.

| F8. Suspension concentrates | a) | b) | c) | d) |
|---|---|---|---|---|
| mixture of a compound of formula A with one of the compounds of formulae I to VII | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |

-continued

| F8. Suspension concentrates | a) | b) | c) | d) |
|---|---|---|---|---|
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compound of formula A and the mixing partner or mixing partners of formulae I to VII to be formulated individually and to be brought together in the applicator in the desired mixing ratio, in the form of a "tank mixture" in water, only shortly before application.

It may also prove advantageous to apply the compound of formula A, if appropriate in combination with a safener, at a different time from one or more of the compounds of formulae I to VII. Also possible is application of the compound of formula A at a different time from one or more of the compounds of formulae I to VII that, if appropriate, is/are in combination with the safener.

BIOLOGICAL EXAMPLES

A synergistic effect exists whenever the action of the active ingredient combination of the compound of formula A and I and/or II and/or III and/or IV and/or V and/or VI and/or VII is greater than the sum of the actions of the compounds when applied individually.

The expected herbicidal action E for a given combination of at least two herbicides can be calculated as follows (see COLBY, S. R., "Calculating synergistic and antagonistic response of herbicide combinations", Weeds 15, pages 20–22, 1967):

$$E = X + \frac{Y \cdot (100 - X)}{100}$$

In the above formula:
X=percentage growth inhibition in the case of treatment with the compound of formula A at a rate of application of p kg per hectare compared with the untreated control (=0%).
Y=percentage herbicidal action in the case of treatment with at least one of the compounds of formulae I to VII at a rate of application of q kg per hectare compared with the untreated control.
E=Expected herbicidal action (percentage herbicidal action compared with the untreated control) after treatment with the compounds of formulae A and I to VII at a rate of application of p+q kg of active ingredient per hectare.

If the action actually observed is greater than the expected action E, then there is synergism. Increases in the action of herbicide combinations from 0–50% herbicidal action (expected value) to 70–100% herbicidal action (observed), and from 90–95% herbicidal action (expected value) to 95–100% herbicidal action (observed) are recognised by the person skilled in the art as being synergistic increases.

The synergistic effect of the combinations of the compound of formula A with at least one of the compounds of formulae I to VII is demonstrated in the following Examples.

The results, together with the expected values, E calculated according to the Colby formula are entered in Tables B1 to B6. Each of the active ingredients used and their rates of application [g active ingredient/ha], and also the weeds and useful plants tested, are indicated.

Example B1

Post-emergence test:

The test plant seeds are grown to the 4- to 6-leaf stage under greenhouse conditions in plastics pots. The culture substrate used is a standard soil. At the 4- to 6-leaf stage the herbicides are applied separately and in admixture to the test plants. The test compounds are applied in the form of an aqueous suspension (Formulation Example F8, c)) in 500 l of water/ha. The rates of application conform to the optimum concentrations ascertained under field conditions and greenhouse conditions. Evaluation of the tests is carried out after 24 days. The following linear scale is used as a measure (% action):

100%=plants have died
50%=moderate action
0%=no phytotoxic action (as untreated control).

Test plants: brachiaria, cyperus, digitaria, echinochloa, panicum.

Examples of the synergistic activity of the combinations of the compound of formula A with the compound of formula III (glyphosate) are given in Table B1.

TABLE B1

Tests with compound of formula A and glyphosate Gly (compound of formula III), separately and in admixture, post-emergence, on 5 weeds. Herbicidal activity in [%] 24 days after application.

| Compound | Rate of application [g active ingredient/ha] | Weed: [%] Brachiaria | E [Expected value] |
|---|---|---|---|
| A | 100 | 10 | |
| Gly | 400 | 70 | |
| A + Gly | 100 + 400 | 90 | 73 |
| A | 100 | 10 | |
| Gly | 300 | 70 | |
| A + Gly | 100 + 300 | 90 | 73 |
| A | 200 | 15 | |
| Gly | 200 | 60 | |
| A + Gly | 200 + 200 | 80 | 66 |

| | | Cyperus | |
|---|---|---|---|
| A | 100 | 60 | |
| Gly | 400 | 15 | |
| A + Gly | 100 + 400 | 95 | 66 |
| A | 50 | 50 | |
| Gly | 400 | 15 | |
| A + Gly | 50 + 400 | 90 | 58 |
| A | 50 | 50 | |
| Gly | 300 | 5 | |
| A + Gly | 50 + 300 | 90 | 53 |

| | | Digitaria | |
|---|---|---|---|
| A | 200 | 90 | |
| Gly | 100 | 25 | |
| A + Gly | 200 + 100 | 98 | 93 |
| A | 100 | 90 | |
| Gly | 100 | 25 | |
| A + Gly | 100 + 100 | 98 | 93 |
| A | 50 | 85 | |
| Gly | 100 | 25 | |
| A + Gly | 50 + 100 | 95 | 88 |

TABLE B1-continued

Tests with compound of formula A and glyphosate Gly (compound of formula III), separately and in admixture, post-emergence, on 5 weeds. Herbicidal activity in [%] 24 days after application.

| | | Echinochloa | |
|---|---|---|---|
| A | 200 | 45 | |
| Gly | 400 | 20 | |
| A + Gly | 200 + 400 | 90 | 56 |
| A | 200 | 45 | |
| Gly | 200 | 0 | |
| A + Gly | 200 + 200 | 80 | 45 |
| A | 100 | 15 | |
| Gly | 400 | 20 | |
| A + Gly | 100 + 400 | 75 | 32 |

| | | Panicum | |
|---|---|---|---|
| A | 200 | 70 | |
| Gly | 100 | 70 | |
| A + Gly | 200 + 100 | 98 | 91 |
| A | 50 | 50 | |
| Gly | 100 | 70 | |
| A + Gly | 50 + 100 | 90 | 85 |

The same results are obtained when the test compounds of formulae A and III are formulated in accordance with Examples F1 to F7.

Example B2

Pre-emergence test:

The test plants are sown in plastics pots in standard soil. Directly after sowing the test compounds are applied by spraying, separately or in admixture, in the form of an aqueous suspension of the test compounds (Formulation Example F8, c) and d)) or in the form of an emulsion concentrate (Formulation Example F1, d)) in 500 l of water/ha. The rates of application conform to the optimum concentrations ascertained under field conditions and greenhouse conditions. The test plants are then cultivated in the greenhouse under optimum conditions. After 34 days' (Tables B2 to B5) and 41 days' (Table B6) test duration, the test is evaluated (% action, 100%=plants have died, 0%=no phytotoxic action). From 61 to 80% (especially from 81 to 100%) phytotoxicity indicates good to very good herbicidal action in weeds; from 0 to 15% (especially from 0 to 5%) phytotoxicity indicates good to very good tolerance in useful plants.

Test plants: abutilon, bidens, euphorbia, ipomoea, sesbamia, xanthium, rottboellia, sida, Sorghum bicolor.

Examples of the synergistic activity of the combinations of the compound of formula A with the compounds of formulae II (terbuthylazine, atrazine) and V (metolachlor racemate, metolachlor S-enantiomer and dimethenamid) are given in Tables B2 to B6.

TABLE B2

Tests on maize with compound of formula A and terbuthylazine Terb (compound of formula II), separately and in admixture, pre-emergence on maize and 5 weeds. Herbicidal activity in [%] 34 days after application. E = expected value.

| Compound | Rate of application [g active ingredient/ha] | Useful plant: [%] Maize | Weed: [%] Abutilon | E |
|---|---|---|---|---|
| A | 30 | 10 | 40 | |
| Terb | 500 | 0 | 90 | |

TABLE B2-continued

Tests on maize with compound of formula A and terbuthylazine Terb (compound of formula II), separately and in admixture, pre-emergence on maize and 5 weeds. Herbicidal activity in [%] 34 days after application. E = expected value.

| | | | | |
|---|---|---|---|---|
| A + Terb | 30 + 500 | 15 | 100 | 94 |
| A | 15 | 0 | 20 | |
| Terb | 500 | 0 | 90 | |
| A + Terb | 15 + 500 | 10 | 100 | 92 |
| A | 15 | 0 | 20 | |
| Terb | 250 | 0 | 30 | |
| A + Terb | 15 + 250 | 5 | 98 | 44 |

| | | Maize | Bidens | |
|---|---|---|---|---|
| A | 60 | 10 | 90 | |
| Terb | 125 | 0 | 0 | |
| A + Terb | 60 + 125 | 0 | 100 | 90 |
| A | 30 | 10 | 30 | |
| Terb | 250 | 0 | 60 | |
| A + Terb | 30 + 250 | 10 | 90 | 72 |
| A | 30 | 10 | 30 | |
| Terb | 125 | 0 | 0 | |
| A + Terb | 30 + 125 | 0 | 95 | 30 |

| | | Maize | Euphorbia | |
|---|---|---|---|---|
| A | 30 | 10 | 90 | |
| Terb | 125 | 0 | 40 | |
| A + Terb | 30 + 125 | 0 | 100 | 94 |
| A | 15 | 0 | 0 | |
| Terb | 500 | 0 | 95 | |
| A + Terb | 15 + 500 | 10 | 100 | 95 |
| A | 15 | 0 | 0 | |
| Terb | 250 | 0 | 70 | |
| A + Terb | 15 + 250 | 5 | 80 | 70 |

| | | Maize | Ipomoea | |
|---|---|---|---|---|
| A | 60 | 10 | 30 | |
| Terb | 125 | 0 | 0 | |
| A + Terb | 60 + 125 | 0 | 50 | 30 |
| A | 30 | 10 | 20 | |
| Terb | 500 | 0 | 95 | |
| A + Terb | 30 + 500 | 15 | 100 | 96 |

| | | Maize | Sesbania | |
|---|---|---|---|---|
| A | 60 | 10 | 50 | |
| Terb | 250 | 0 | 80 | |
| A + Terb | 60 + 250 | 10 | 100 | 90 |

TABLE B3

Tests on maize with compound of formula A and atrazine Atra (compound of formula II), separately and in admixture, pre-emergence on maize and 5 weeds. Herbicidal activity in [%] 34 days after application. E = expected value.

| Compound | Rate of application [g active ingredient/ha] | Useful plant: [%] Maize | Weed: [%] Abutilon | E |
|---|---|---|---|---|
| A | 30 | 10 | 40 | |
| Atra | 125 | 0 | 0 | |
| A + Atra | 30 + 125 | 0 | 90 | 40 |
| A | 15 | 0 | 20 | |
| Atra | 500 | 0 | 98 | |
| A + Atra | 15 + 500 | 0 | 100 | 98 |

| | | Maize | Bidens | |
|---|---|---|---|---|
| A | 60 | 10 | 90 | |
| Atra | 125 | 0 | 60 | |
| A + Atra | 60 + 125 | 10 | 100 | 96 |
| A | 30 | 10 | 30 | |

TABLE B3-continued

Tests on maize with compound of formula A and atrazine Atra (compound of formula II), separately and in admixture, pre-emergence on maize and 5 weeds. Herbicidal activity in [%] 34 days after application. E = expected value.

| | | | | |
|---|---|---|---|---|
| Atra | 125 | 0 | 60 | |
| A + Atra | 30 + 125 | 0 | 100 | 72 |
| A | 15 | 0 | 20 | |
| Atra | 125 | 0 | 60 | |
| A + Atra | 15 + 125 | 0 | 98 | 68 |

| | | Maize | Euphorbia | |
|---|---|---|---|---|
| A | 30 | 10 | 90 | |
| Atra | 125 | 0 | 0 | |
| A + Atra | 30 + 125 | 0 | 100 | 90 |

| | | Maize | Ipomoea | |
|---|---|---|---|---|
| A | 60 | 10 | 30 | |
| Atra | 250 | 0 | 70 | |
| A + Atra | 60 + 250 | 10 | 100 | 79 |
| A | 60 | 10 | 30 | |
| Atra | 125 | 0 | 0 | |
| A + Atra | 60 + 125 | 10 | 60 | 30 |

| | | Maize | Xanthium | |
|---|---|---|---|---|
| A | 30 | 10 | 0 | |
| Atra | 250 | 0 | 0 | |
| A + Atra | 30 + 250 | 0 | 70 | 0 |
| A | 15 | 0 | 0 | |
| Atra | 500 | 0 | 95 | |
| A + Atra | 15 + 500 | 0 | 100 | 95 |

TABLE B4

Tests on maize with compound of formula A and metolachlor racemic Met. rac. (compound of formula V), separately and in admixture, pre-emergence on maize and 7 weeds. Herbicidal activity in [%] 34 days after application. E = expected value.

| Compound | Rate of application [g active ingredient/ha] | Useful plant: [%] Maize | Weed: [%] Abutilon | E |
|---|---|---|---|---|
| A | 30 | 10 | 40 | |
| Met.rac. | 1000 | 0 | 20 | |
| A + Met.rac. | 30 + 1000 | 0 | 98 | 52 |
| A | 30 | 10 | 40 | |
| Met.rac. | 500 | 0 | 20 | |
| A + Met.rac. | 30 + 500 | 0 | 100 | 52 |

| | | Maize | Bidens | |
|---|---|---|---|---|
| A | 30 | 10 | 30 | |
| Met.rac. | 1000 | 0 | 30 | |
| A + Met.rac. | 30 + 1000 | 0 | 90 | 51 |

| | | Maize | Euphorbia | |
|---|---|---|---|---|
| A | 30 | 10 | 90 | |
| Met.rac. | 500 | 0 | 0 | |
| A + Met.rac. | 30 + 500 | 0 | 95 | 90 |
| A | 15 | 0 | 0 | |
| Met.rac. | 500 | 0 | 0 | |
| A + Met.rac. | 15 + 500 | 0 | 90 | 0 |

| | | Maize | Ipomoea | |
|---|---|---|---|---|
| A | 60 | 10 | 30 | |
| Met.rac. | 1000 | 0 | 0 | |
| A + Met.rac. | 60 + 1000 | 0 | 60 | 30 |

TABLE B4-continued

Tests on maize with compound of formula A and metolachlor racemic Met. rac. (compound of formula V), separately and in admixture, pre-emergence on maize and 7 weeds. Herbicidal activity in [%] 34 days after application. E = expected value.

|  |  | Maize | Rottboellia |  |
|---|---|---|---|---|
| A | 60 | 10 | 30 |  |
| Met.rac. | 1000 | 0 | 0 |  |
| A + Met.rac. | 60 + 1000 | 0 | 80 | 30 |

|  |  | Maize | Sesbania |  |
|---|---|---|---|---|
| A | 60 | 10 | 50 |  |
| Met.rac. | 1000 | 0 | 60 |  |
| A + Met.rac. | 60 + 1000 | 0 | 100 | 70 |

|  |  | Maize | Sida |  |
|---|---|---|---|---|
| A | 15 | 0 | 80 |  |
| Met.rac. | 500 | 0 | 50 |  |
| A + Met.rac. | 15 + 500 | 0 | 95 | 90 |
| A | 15 | 0 | 80 |  |
| Met.rac. | 250 | 0 | 0 |  |
| A + Met.rac. | 15 + 250 | 0 | 100 | 80 |

TABLE B5

Tests on maize with compound of formula A and metolachlor S-enantiomer Met-S (compound of formula V), separately and in admixture, pre-emergence on maize and 6 weeds. Herbicidal activity in [%] 34 days after application. E = expected value.

| Compound | Rate of application [g active ingredient/ha] | Useful plant: [%] Maize | Weed: [%] Abutilon | E |
|---|---|---|---|---|
| A | 30 | 10 | 40 |  |
| Met-S | 300 | 10 | 10 |  |
| A + Met-S | 30 + 300 | 5 | 100 | 46 |
| A | 30 | 10 | 40 |  |
| Met-S | 150 | 0 | 0 |  |
| A + Met-S | 30 + 150 | 0 | 100 | 40 |

|  |  | Maize | Brachiaria |  |
|---|---|---|---|---|
| A | 60 | 10 | 60 |  |
| Met-S | 300 | 10 | 50 |  |
| A + Met-S | 60 + 300 | 10 | 100 | 80 |
| A | 60 | 10 | 60 |  |
| Met-S | 150 | 0 | 20 |  |
| A + Met-S | 60 + 150 | 0 | 75 | 68 |

|  |  | Maize | Euphorbia |  |
|---|---|---|---|---|
| A | 30 | 10 | 90 |  |
| Met-S | 600 | 10 | 0 |  |
| A + Met-S | 30 + 600 | 15 | 95 | 90 |
| A | 15 | 0 | 0 |  |
| Met-S | 300 | 10 | 0 |  |
| A + Met-S | 15 + 300 | 5 | 70 | 0 |
| A | 15 | 0 | 0 |  |
| Met-S | 150 | 0 | 0 |  |
| A + Met-S | 15 + 150 | 0 | 70 | 0 |

|  |  | Maize | Sida |  |
|---|---|---|---|---|
| A | 15 | 0 | 80 |  |
| Met-S | 300 | 10 | 40 |  |
| A + Met-S | 15 + 300 | 5 | 100 | 88 |
| A | 15 | 0 | 80 |  |
| Met-S | 150 | 0 | 0 |  |
| A + Met-S | 15 + 150 | 0 | 100 | 80 |

TABLE B5-continued

Tests on maize with compound of formula A and metolachlor S-enantiomer Met-S (compound of formula V), separately and in admixture, pre-emergence on maize and 6 weeds. Herbicidal activity in [%] 34 days after application. E = expected value.

|  |  | Maize | Xanthium |  |
|---|---|---|---|---|
| A | 60 | 10 | 20 |  |
| Met-S | 600 | 10 | 20 |  |
| A + Met-S | 60 + 600 | 10 | 80 | 36 |
| A | 60 | 10 | 20 |  |
| Met-S | 300 | 10 | 0 |  |
| A + Met-S | 60 + 300 | 10 | 60 | 20 |

TABLE B6

Tests on maize with compound of formula A and dimethenamid Dime (compound of formula V), separately and in admixture, pre-emergence on maize and 6 weeds. Herbicidal activity in [%] 41 days after application. E = expected value.

| Compound | Rate of application [g active ingredient/ha] | Useful plant: [%] Maize | Weed: [%] Abutilon | E |
|---|---|---|---|---|
| A | 15 | 0 | 80 |  |
| Dime | 250 | 0 | 10 |  |
| A + Dime | 15 + 250 | 0 | 100 | 82 |
| A | 8 | 0 | 50 |  |
| Dime | 250 | 0 | 10 |  |
| A + Dime | 8 + 250 | 0 | 70 | 55 |

|  |  | Maize | Euphorbia |  |
|---|---|---|---|---|
| A | 15 | 0 | 85 |  |
| Dime | 500 | 0 | 30 |  |
| A + Dime | 15 + 500 | 0 | 100 | 90 |

|  |  | Maize | Ipomoea |  |
|---|---|---|---|---|
| A | 30 | 10 | 0 |  |
| Dime | 1000 | 20 | 0 |  |
| A + Dime | 30 + 1000 | 20 | 70 | 0 |

|  |  | Maize | Rottboellia |  |
|---|---|---|---|---|
| A | 60 | 40 | 70 |  |
| Dime | 125 | 0 | 20 |  |
| A + Dime | 60 + 125 | 15 | 100 | 76 |
| A | 30 | 40 | 80 |  |
| Dime | 125 | 0 | 20 |  |
| A + Dime | 30 + 125 | 10 | 100 | 84 |

|  |  | Maize | Sida |  |
|---|---|---|---|---|
| A | 8 | 0 | 40 |  |
| Dime | 1000 | 20 | 95 |  |
| A + Dime | 8 + 1000 | 0 | 100 | 97 |
| A | 8 | 0 | 40 |  |
| Dime | 500 | 0 | 85 |  |
| A + Dime | 8 + 500 | 0 | 100 | 91 |
| A | 8 | 0 | 40 |  |
| Dime | 250 | 0 | 40 |  |
| A + Dime | 8 + 250 | 0 | 100 | 64 |

|  |  | Maize | Sorghum bic. |  |
|---|---|---|---|---|
| A | 8 | 0 | 0 |  |
| Dime | 1000 | 20 | 80 |  |
| A + Dime | 8 + 1000 | 0 | 100 | 80 |

The same results are obtained when the test compounds of formulae A and II and V are formulated in accordance with Examples F2 to F7.

The compositions according to the invention demonstrate pronounced synergistic effects, both post- and preemergence, in various mixing ratios of the individual components and at various rates of application of the mixtures on different weeds (monocotyledons and dicotyledons).

Synergistic increases in activity in the upper spectrum of herbicidal activity are especially valuable from an economic standpoint when, for example, an expected herbicidal value (E) of 90–95% can be increased to an observed herbicidal action of 95–100%, as can be obtained, for example, in euphorbia in Table B6 with compound of formula A and dimethenamide Dime in a mixture of 15+500 g of active ingredient/ha.

Similarly markedly selective herbicidal activities are demonstrated also by the following compositions according to the invention:

compound of formula A+atrazine+metolachlor S-enantiomer; compound of formula A+terbuthylazine+metolachlor S-enantiomer; compound of formula A+metolachlor racemate+benoxacor; compound of formula A+metolachlor S-enantiomer+benoxacor; compound of formula A+glufosinate; compound of formula A+sulfosate; compound of formula A+ametryn; and compound of formula A+fluthiacet.

What is claimed is:

1. A synergistic herbicidal that comprises, in admixture with one another, a compound of formula A (A)

or an agrochemically acceptable salt thereof and at least one compound from the substance classes of formula I

A—SO₂—NH—E     (I)

wherein

A is a radical of formula (A1), (A2), (A3), (A4), (A5), (A6), (A7), (A8), (A9), (A10), (A11), (A12), or (A13) and E is a radical of formula (E1) 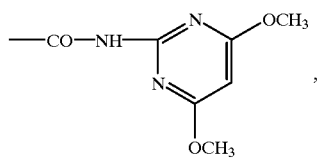, (E2) 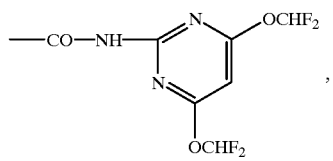, (E3) 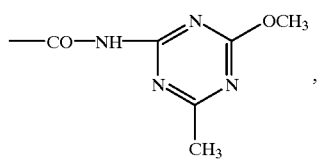, (E4) 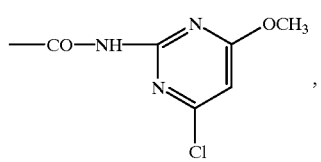, (E5) 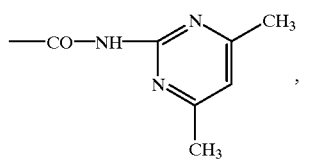, (E6) 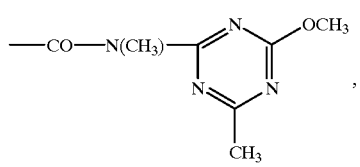, (E7) 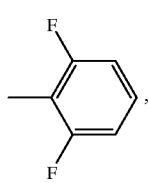, (E8) 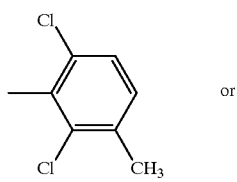 or (E9) 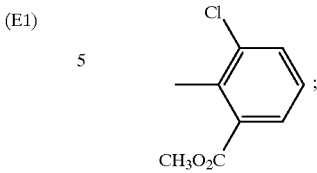;

of formula II

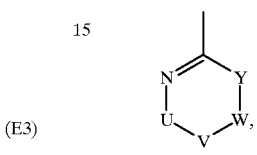 (II)

wherein
U-V is a radical of formula $CR_1=N$, $N=CR_1$ or $NR_1CO$ wherein
$R_1$ is $-NH_2$, $-NHC_3H_7-i$, $-NHC(CH_3)_2CN$, $-NHC_4H_9-t$, $-NHC_2H_5$, $-SCH_3$, $-CH_3$, $-Cl$, $C_6H_{11}$,

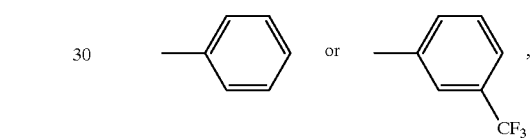

W-Y is a radical of formula $CR_2=N$, $N=CR_2$, $NR_2CO$, NH or $CR_2=CR_3$ wherein
$R_2$ is hydrogen, $-Cl$, $-NH_2$, $-NHC_3H_7-i$, $-NHC_2H_5$ or $-NHC(CH_3)_3$ and
$R_3$ is $-NH_2$, $-NHCH_3$ or $-O-CO-SC_8H_{17}$, and
R is $-Cl$, $-SCH_3$, $-C_4H_9-t$,

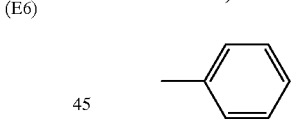

or hydrogen;
of formula III

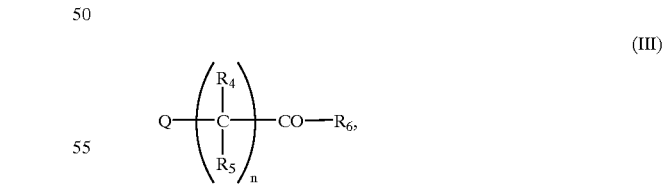 (III)

wherein
n is 0 or 1,
$R_4$ is hydrogen,
$R_5$ is hydrogen, $-CH_3$ or $-NH_2$,
$R_6$ is hydroxy, $-OC_2H_5$, $-O-C(CH_3)_2-CO_2C_2H_5$, $-NHSO_2CH_3$, $-OCH_3$, $-OC_4H_9-n$, $-OCH_2-C\equiv CH$ or $-OC_2H_4-O-N=C(CH_3)_2$ and Q is a radical of formula
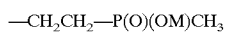 (Q1)
or
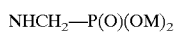 (Q2)
wherein M is an alkali metal, ammonium, alkylammonium, sulfonium or alkylsulfonium,
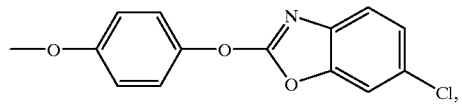 (Q3)
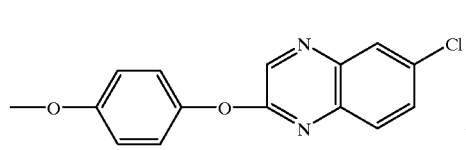 (Q4)
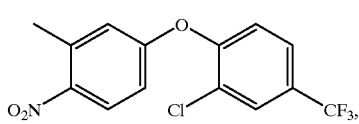 (Q5)
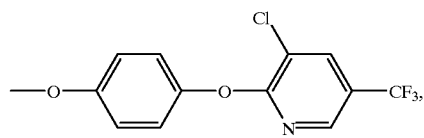 (Q6)
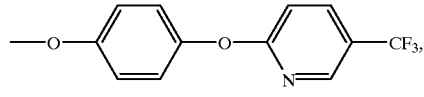 (Q7)
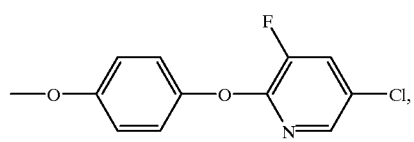 (Q8)
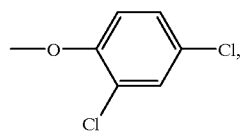 (Q9)
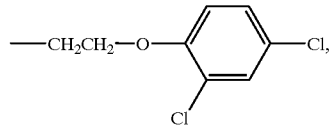 (Q10)
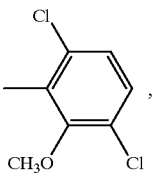 (Q11)
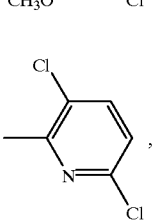 (Q12)
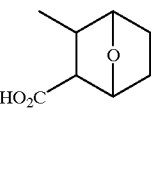 (Q13)
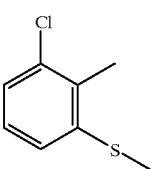 (Q14)
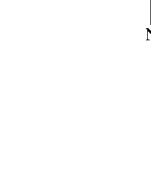 (Q15)
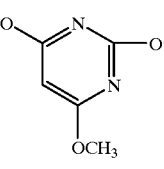 (Q16)
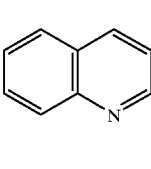 (Q17)

-continued (Q18)
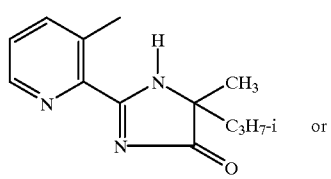
or (Q19)
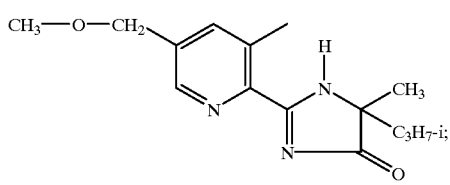

of formula IV

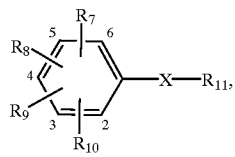 (IV)

wherein $R_7$ is 2-$NO_2$, 2-Br or 2-F, $R_8$ is 6-$NH_2$, 6-Br or 6-$NO_2$, or $R_8$ and $R_7$ together form a radical of formula —C($CH_3$)$_2$—CH(O$C_2H_5$)O— that bridges the 2- and 3-positions of the phenyl radical, the carbon atom of that radical being linked to the 2-position and the oxygen atom of that radical being linked to the 3-position, $R_9$ is 3-$CH_3$, 4-$CF_3$, 4-CN or 5-$SCH_2COOCH_3$, $R_{10}$ is hydrogen, 4-$CH_3$ or 4-Cl, X is —O—, —NH—, —N$C_3H_7$(n)— or —N$C_2H_5$— and $R_{11}$ is hydrogen, —CH($C_2H_5$)$_2$, —$C_3H_7$—n, —$CH_2$—C($CH_3$)=$CH_2$, —CO—$C_8H_{17}$—n, —CO—$C_7H_{15}$—n or —$SO_2CH_3$, or $R_{11}$ and X together form a radical

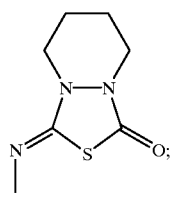

of formula V

Z—N(R$_{12}$)—CO—R$_{13}$, (V)

wherein

Z is a radical of formula

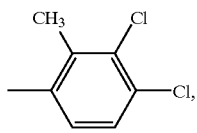 (Z1)

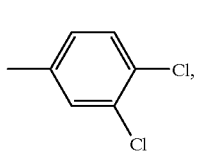 (Z2)

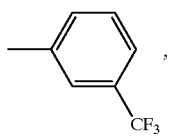 (Z3)

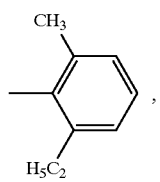 (Z4)

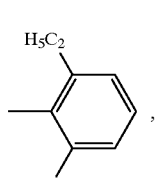 (Z5)

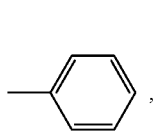 (Z6)

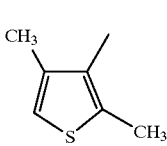 (Z7)

—$CH_2$—$C_3H_7$-i, (Z8)

—$C_3H_7$-n, (Z9)

—$C_4H_9$-n, (Z10)

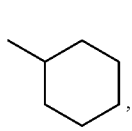 (Z11)

-continued (Z12)
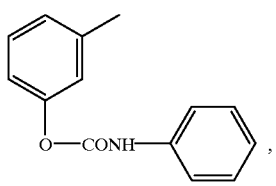

(Z13)
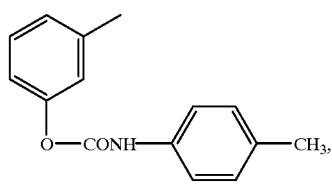

(Z14)
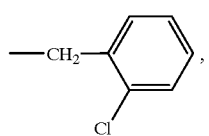

(Z15)
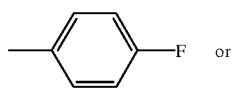 or (Z16)
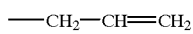

(Z17)
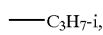

$R_{12}$ is hydrogen, —$CH_2OCH_3$, —$CH_2OC_2H_5$, —$CH(CH_3)CH_2OCH_3$, —$C_3H_7$—i, —$CH_2$—$C_3H_7$—i, —$C_3H_7$—n, —$CH_3$, —$C_2H_5$ or —$CH_2$—CH=$CH_2$ or $R_{12}$ forms together with Z a radical of formula

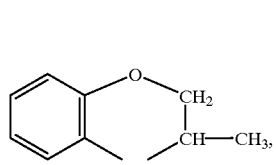 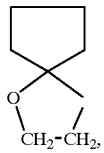

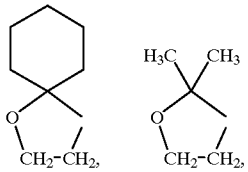 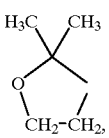 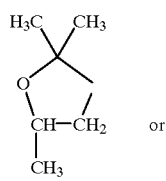 or

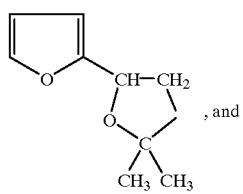, and $R_{13}$ is —$N(CH_3)_2$, —$N(OCH_3)CH_3$, —$CH_2Cl$, —$CHCl_2$, —$SC_2H_5$, —$SC_3H_7$—n, —$OCH_3$, —$OC_2H_5$, —$CH_2$—CH=$CH_2$ or

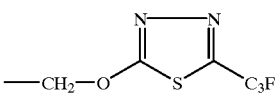

or $R_{13}$ forms together with $R_{12}$ a radical of formula —O—$CH_2$—$C(CH_3)_2$—, —$CH_2$—CH($CH_2$Cl)—CHCl— or

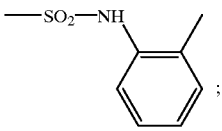;

of formula VI (VI)
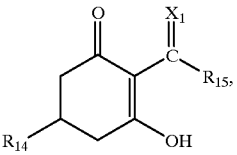

wherein
$R_{14}$ is hydrogen or —$CH_2$—CH($CH_3$)—$SC_2H_5$,
$R_{15}$ is —$C_2H_5$, —$C_3H_7$—n or

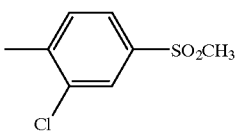

and
$X_1$ is =O, =$NOC_2H_5$ or =$NOCH_2$—CH=CHCl;
or of formula VII (VII)
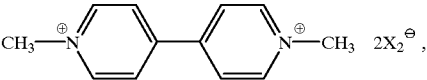

where
$X_2^\ominus$ is $Cl^\ominus$ or $CH_3SO_3^\ominus$.

2. A composition according to claim 1, wherein in the compounds selected of formula II $R_1$ is
—$NHC_3H_7$—i, —$NHC(CH_3)_2CN$, —$NHC_4H_9$—t, —$NHC_2H_5$, —$SCH_3$, —$CH_3$, —Cl,

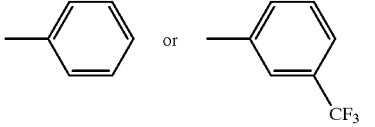

W-Y is a radical of formula $CR_2$=N, N=$CR_2$, $NR_2CO$ or $CR_2$=$CR_3$.

3. A composition according to claim 1 that comprises at least one compound selected from the group consisting of formula I
$$A—SO_2—NH—E \quad (I),$$
wherein
A is a radical of formula
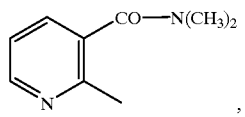 (A1)
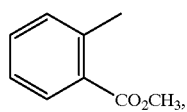 (A2)
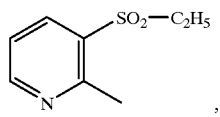 (A3)
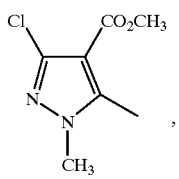 (A4)
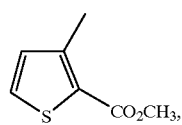 (A5)
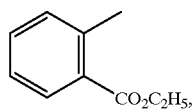 (A6)
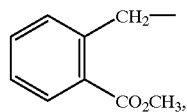 (A7)
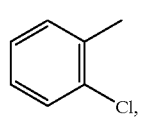 (A8)
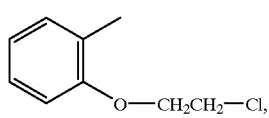 (A9)
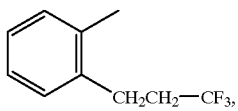 (A10)
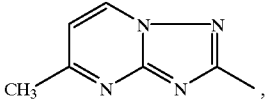 (A11)
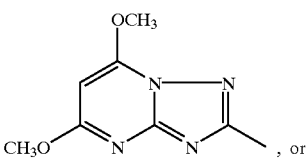 (A12)
, or
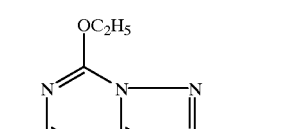 (A13)
and
E is a radical of formula
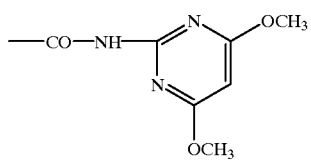 (E1)
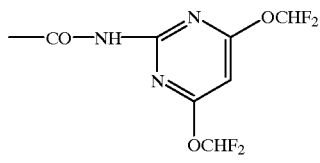 (E2)
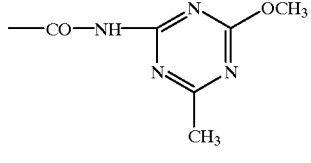 (E3)
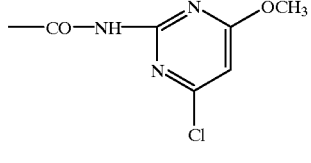 (E4)
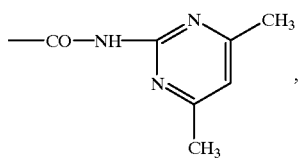 (E5)

-continued

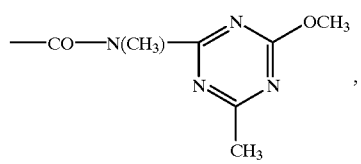
(E6)

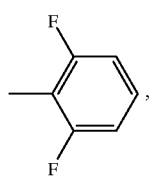
(E7)

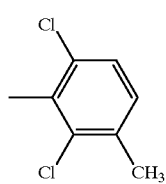
(E8)

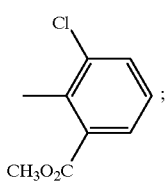
(E9)

of formula II

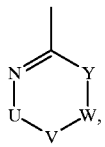
(II)

wherein

U-V is a radical of formula $CR_1$=N or N=$CR_1$ wherein $R_1$ is —$NHC_3H_7$—i, —$NHC(CH_3)_2CN$, —$NHC_4H_9$—t, —$NHC_2H_5$ or —Cl, W-Y is a radical of formula $CR_2$=N, N=$CR_2$ or $CR_2$=$CR_3$ wherein
$R_2$ is hydrogen, —$NHC_3H_7$—i, —$NHC_2H_5$ or —$NHC(CH_3)_3$ and
$R_3$ is —O—CO—$SC_8H_{17}$, and R is —Cl, —$SCH_3$ or

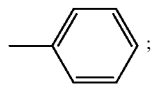;

of formula II

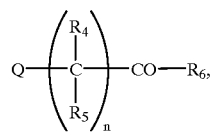
(III)

wherein
n is 0 or 1,
$R_4$ is hydrogen,
$R_5$ is hydrogen, —$CH_3$ or —$NH_2$,
$R_6$ is hydroxy, —$OC_2H_5$, —$OC_4H_9$—n or —$OC_2H_4$—O—N=$C(CH_3)_2$ and
Q is a radical of formula

—$CH_2CH_2$—P(O)(OM)$CH_3$   (Q1)

or $NHCH_2$—P(O)(OM)$_2$   (Q2)

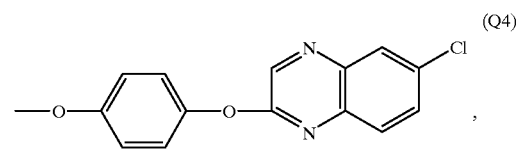
(Q4)

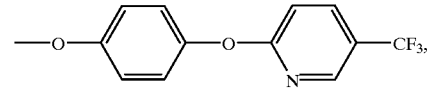
(Q7)

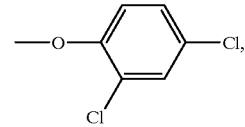
(Q9)

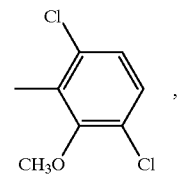
(Q11)

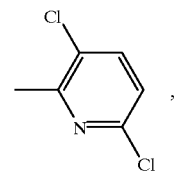
(Q12)

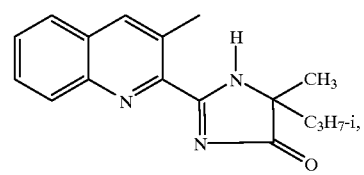
(Q16)

-continued

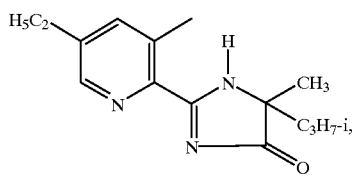 (Q17)

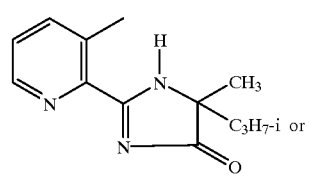 (Q18)

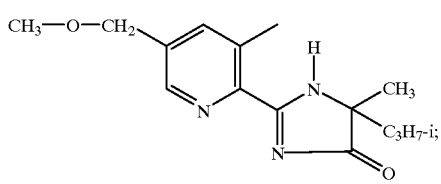 (Q19)

of formula IV

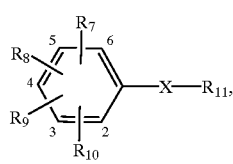 (IV)

wherein

R$_7$ is 2-NO$_2$ or 2-Br,
R$_8$ is 6-NH$_2$ or 6-Br,
R$_9$ is 3-CH$_3$, 4-CF$_3$ or 4-CN,
R$_{10}$ is 4-CH$_3$,
X is —O—, —NH— or —NC$_3$H$_7$—n and
R$_{11}$ is hydrogen, —CH(C$_2$H$_5$)$_2$ or —C$_3$H$_7$—n;

of formula V

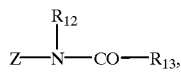 (V)

wherein

Z is a radical of formula

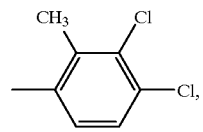 (Z1)

-continued

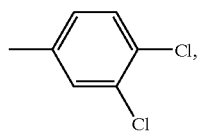 (Z2)

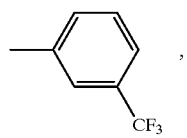 (Z3)

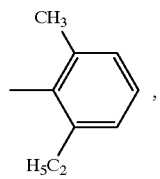 (Z4)

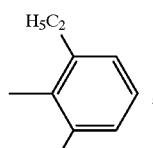 (Z5)

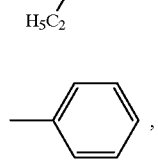 (Z6)

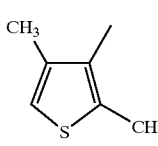 (Z7)

—CH$_2$—C$_3$H$_7$-i, (Z8)

—C$_3$H$_7$-n, (Z9)

—C$_4$H$_9$-n, (Z10)

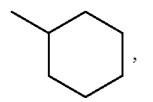 (Z11)

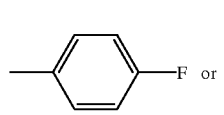 (Z15)

—C$_3$H$_7$-i, (Z16)

R$_{12}$ is hydrogen, —CH$_2$OCH$_3$, —CH$_2$OC$_2$H$_5$, —CH(CH$_3$)CH$_2$OCH$_3$, —C$_3$H$_7$—i, —CH$_2$—C$_3$H$_7$—i, —C$_3$H$_7$—n, —CH$_3$, —C$_2$H$_5$ or —CH$_2$—CH=CH$_2$ or $R_{12}$ forms together with Z a radical of formula

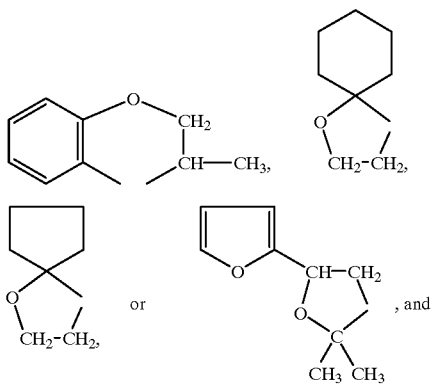

and $R_{13}$ is —N(CH$_3$)$_2$, —N(OCH$_3$)CH$_3$, —CH$_2$Cl, —CHCl$_2$, —SC$_2$H$_5$, —SC$_3$H$_7$—n, —OCH$_3$, —OC$_2$H$_5$, —CH$_2$—CH—CH$_2$ or

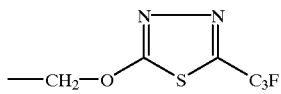

or $R_{13}$ forms together with $R_{12}$ a radical of formula —O—CH$_2$—C(CH$_3$)$_2$—, —CH$_2$—CH(CH$_2$Cl)—CHCl— or

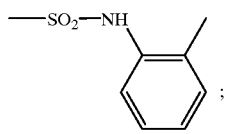

of formula VI

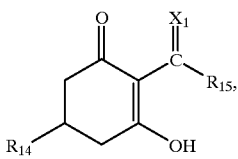

(VI)

wherein $R_{14}$ is hydrogen, $R_{15}$ is —C$_3$H$_7$—n or

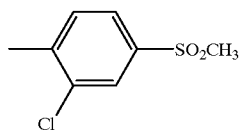

and $X_1$ is =O or =NOC$_2$H$_5$;

or of formula VII

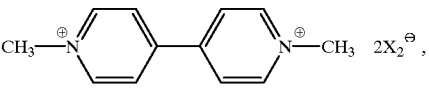

(VII)

wherein $X_2^\ominus$ is Cl$^\ominus$ or CH$_3$SO$_3^\ominus$.

4. A composition according to claim 3 that comprises as active ingredient combination:

compound of formula A+atrazine, compound of formula A+fluthiacet, compound of formula A+cyanazine, compound of formula A+flumetsulam, compound of formula A+metolachlor (racemate), compound of formula A+metolachlor (S-enantiomer), compound of formula A+metosulam, compound of formula A+nicosulfuron, compound of formula A+pendimethalin, compound of formula A+rimsulfuron, compound of formula A+terbuthylazine, compound of formula A+2,4-D, compound of formula A+bromoxynil, compound of formula A+dicamba, compound of formula A+halosulfuron, compound of formula A+primisulfuron, compound of formula A+prosulfuron, compound of formula A+simazine, compound of formula A+sulcotrione, compound of formula A+acetochlor, compound of formula A+alachlor, compound of formula A+ametryn, compound of formula A+bentazon, compound of formula A+butylate, compound of formula A+clopyralid, compound of formula A+dimethenamid (racemate), compound of formula A+dimethenamid (S-enantiomer), compound of formula A+EPTC, compound of formula A+thifensulfuron, compound of formula A+trifluralin, compound of formula A+cloransulam-methyl, compound of formula A+terbutryn, compound of formula A+glyphosate, compound of formula A+glufosinate or compound of formula A+sulfosate.

5. A composition according to claim 4 that comprises as active ingredient combination:

compound of formula A+primisulfuron+dicamba, compound of formula A+prosulfuron+dicamba, compound of formula A+primisulfuron+bromoxynil, compound of formula A+primisulfuron+pyridate, compound of formula A+prosulfuron+bromoxynil, compound of formula A+atrazine+metolachlor (S-enantiomer), compound of formula A+terbuthylazine+metolachlor (S-enantiomer) or compound of formula A+prosulfuron+pyridate.

6. A composition according to claim 1 that comprises as active ingredient combination:

compound of formula A+atrazine, compound of formula A+cyanazine, compound of formula A+flumetsulam, compound of formula A+metolachlor (racemate), compound of formula A+metolachlor (S-enantiomer), compound of formula A+metosulam, compound of formula A+pendimethalin, compound of formula A+simazine, compound of formula A+terbuthylazine, compound of formula A+acetochlor, compound of formula A+alachlor, compound of formula A+dimethenamid, compound of formula A+cloransulam-methyl, compound of formula A+glyphosate, compound of formula A+glufosinate or compound of formula A+sulfosate.

7. A composition according to claim 1 that comprises as active ingredient combination:

compound of formula A+atrazine+metolachlor S-enantiomer, compound of formula A+terbuthylazine+metolachlor S-enantiomer, compound of formula A+metolachlor racemate+benoxacor, compound of formula A+metolachlor S-enantiomer+benoxacor, compound of formula A+glufosinate, compound of formula A+sulfosate, compound of formula A+ametryn or compound of formula A+fluthiacet.

8. A composition according to claim 6 that comprises as active ingredient combination:

compound of formula A+metolachlor (racemate)+compound of formula V $$Z-N(R_{12})-CO-R_{13}, \quad (V)$$

wherein

Z is —CH$_2$—CH=CH$_2$, R$_{12}$ is —CH$_2$—CH=CH$_2$ or R$_{12}$ forms together with Z a radical of formula

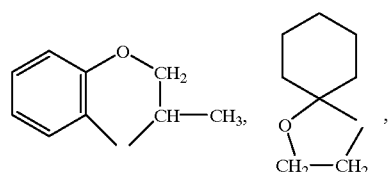

or

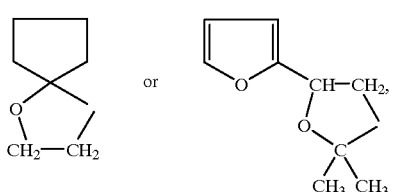

and R$_{13}$ is —CHCl$_2$; compound of formula A+metolachlor (S-enantiomer)+compound of formula V $$Z-N(R_{12})-CO-R_{13}, \quad (V)$$

wherein

Z is —CH$_2$—CH=CH$_2$, R$_{12}$ is —CH$_2$—CH=CH$_2$ or R$_{12}$ forms together with Z a radical of formula

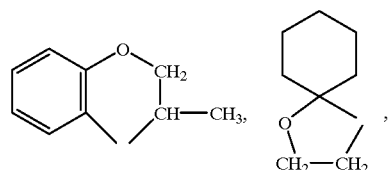

and R$_{13}$ is —CHCl$_2$; compound of formula A+acetochlor+compound of formula V $$Z-N(R_{12})-CO-R_{13}, \quad (V)$$

wherein

Z is —CH$_2$—CH—CH$_2$, R$_{12}$ is —CH$_2$CH=CH$_2$ or R$_{12}$ forms together with Z a radical of formula

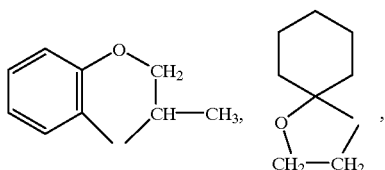

or

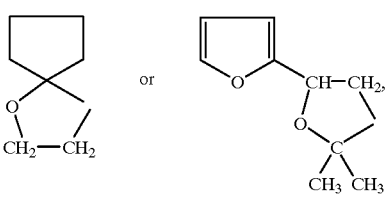

and R$_{13}$ is —CHCl$_2$; or compound of formula A+dimethenamid+compound of formula V $$Z-N(R_{12})-CO-R_{13}, \quad (V)$$

wherein

Z is —CH$_2$—CH=CH$_2$, R$_{12}$ is —CH$_2$—CH=CH$_2$ or R$_{12}$ together with Z forms a radical of formula

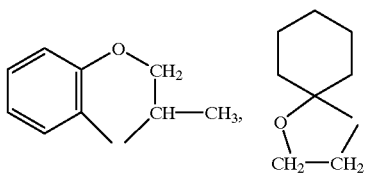

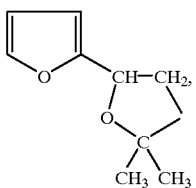

and R$_{13}$ is —CHCl$_2$.

9. A composition according to claim 4 that comprises as active ingredient combination:
compound of formula A+EPIC+compound of formula V

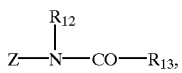

wherein
Z is —CH$_2$—CH—CH$_2$, R$_{12}$ is —CH$_2$—CH=CH$_2$ or R$_{12}$ forms together with Z a radical of formula

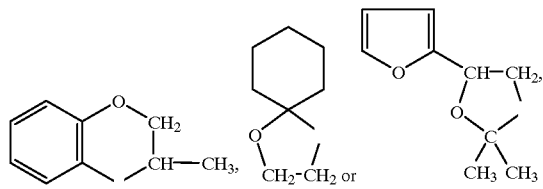

and R$_{13}$ is —CHCl$_2$; or compound of formula A+butylate+compound of formula V

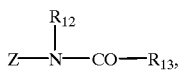

wherein
Z is —CH$_2$—CH=CH$_2$, R$_{12}$ is —CH$_2$—CH=CH$_2$ or R$_{12}$ forms together with Z a radical of formula

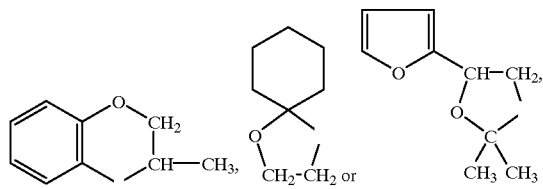

and R$_{13}$ is —CHCl$_2$.

10. A composition according to claim 3 that comprises as active ingredient combination:
compound of formula A+imazaquin, compound of formula A+imazethapyr, compound of formula A+glyphosate, compound of formula A+glufosinate, compound of formula A+sulfosate, compound of formula A+chlorimuron ethyl, compound of formula A+imazapyr, compound of formula A+bensulfuron, compound of formula A+chlorsulfuron, compound of formula A+metsulfuron methyl, compound of formula A+sulfometuron methyl, compound of formula A+triasulfuron or compound of formula A+tribenuron methyl.

11. A composition according to claim 3 that comprises as active ingredient combination:
compound of formula A+imazaquin or compound of formula A+imazethapyr.

12. A composition according to claim 3 that comprises as active ingredient combination:
compound of formula A+fluthiacet, compound of formula A+ametryn, compound of formula A+glufosinate, compound of formula A+glyphosate, compound of formula A+sulfosate or compound of formula A+paraquat.

13. A composition according to claim 3 that comprises as active ingredient combination:
compound of formula A+sethoxydim, compound of formula A+propaquizafop, compound of formula A+quizalofop or compound of formula A+fluazifop.

14. A composition according to claim 1 that comprises the compound of formula A in a ratio by weight of from 1:100 to 1:0.001 with respect to at least one of the compounds from the groups of formulae I to VII.

15. A method of controlling undesired plant growth in crops of useful plants that comprises applying a herbicidally effective amount of a composition according to claim 1 to the crop plant, seed or locus thereof.

16. The method according to claim 15 that comprises applying the compound of formula A to the crop plant, seed or locus thereof at a different time from at least one compound of formulae I to VII.

17. A method according to claim 16 that comprises applying at different times the compounds of the following compositions: compound of formula A+atrazine+metolachlor S-enantiomer, compound of formula A+terbuthylazine+metolachlor S-enantiomer, compound of formula A+metolachlor racemate+benoxacor, compound of formula A+metolachlor S-enantiomer+benoxacor, compound of formula A+glufosinate, compound of formula A+sulfosate, compound of formula A+ametryn or compound of formula A+fluthiacet to the crop plant, seed or the locus thereof.

18. A method according to claim 15 wherein the crop plants are plantation crops, sugar cane, cotton, potatoes, cereals and maize.

19. A method according to claim 15, wherein the crops of useful plants are treated with the said composition at rates of application that correspond to a total amount of active ingredient of from 0.5 to 4.0 kg per hectare.

20. A method of controlling undesired plant growth in crops of useful plants comprising applying a herbicidally effective amount of a composition according to claim 8 to the crop plant, seed or locus thereof.

21. A composition according to claim 8 that comprises as active ingredient combination:
a compound of formula A+metolachlor (racemate)+benoxacor or a compound of formula A+metolachlor (S-enatiomer)+benoxacor.

* * * * *